United States Patent [19]
Herlyn et al.

[11] Patent Number: 5,470,571
[45] Date of Patent: Nov. 28, 1995

[54] METHOD OF TREATING HUMAN EGF RECEPTOR-EXPRESSING GLIOMAS USING RADIOLABELED EGF RECEPTOR-SPECIFIC MAB 425

[75] Inventors: Meenhard Herlyn, Wynnwood; Ulrich Rodeck, Philadelphia, both of Pa.

[73] Assignee: The Wistar Institute, Philadelphia, Pa.

[21] Appl. No.: 513,668

[22] Filed: Apr. 24, 1990

Related U.S. Application Data

[63] Continuation of Ser. No. 149,100, Jan. 27, 1988, abandoned.
[51] Int. Cl.$^6$ .................. A61K 51/10; A61K 39/395; C07K 16/30
[52] U.S. Cl. .................. 424/1.49; 530/388.22; 424/138.1; 424/141.1; 424/143.1; 424/9.1
[58] Field of Search .................. 530/387, 338.22; 435/240.27; 424/85.8, 1.1, 9, 1.49, 138.1, 141.1, 143.1

[56] References Cited

FOREIGN PATENT DOCUMENTS 8503357  8/1985  WIPO .

OTHER PUBLICATIONS

Gooi et al, Molecular Immunology, 1985, vol. 22, pp. 689–693.
Gooi, Bioscience Reports, 1983, vol. 3, pp. 1045–1052.
Gooi et al, Bioscience Reports, 1985, vol. 5, pp. 83–94.
Le Pendu et al, Carbohydrate Research, 1985, vol. 141, pp. 347–349.
Parker et al, Journal of Biological Chemistry, 1984, vol. 259, pp. 9906–9912.
Richert et al, Federation Proceedings, 1983, vol. 42, p. 1904, Abstract No. 859.
Kawamoto et al, Proceedings of the National Academy of Sciences USA, 1983, vol. 80, pp. 1337–1341.
Fernandez-Pol, Journal of Biological Chemistry, 1985, vol. 260, pp. 5003–5011.
Schreiber et al, Journal of Biological Chemistry, 1983, vol. 258, pp. 846–853.
Koprowski et al, Somatic Cell and Molecular Genetics, 1985, vol. 11, pp. 297–302.
Parsons Chandler et al, J. Biol. Chem., 1988, vol. 260, pp. 3360–3362.
Greiner et al, Science, 1987, vol. 235, pp. 895–898.
Fellous et al, European Journal of Immunology, 1979, vol. 9, pp. 446–449.
Greiner et al, Cancer Research, 1984, vol. 44, pp. 3208–3214.
Cohen et al, Journal of Biological Chemistry, 1982, vol. 257, pp. 1523–1531.
Haigler et al, Biochimica et Biophysica Acta, 1980, vol. 598, pp. 314–325.
Libermann et al, Cancer Research, 1984, vol. 44, pp. 753–760.
Ullrich et al, Nature, 1984, vol. 309, pp. 418–425.
Rodeck et al, Cancer Research, 1987, vol. 47, pp. 3692–3696.
Takahashi et al, Cancer Research, 1987, vol. 47, pp. 3847–3850.
Basu et al, Cancer Research, 1987, vol. 47, pp. 2531–2536.
Schreiber et al, Proceedings of the National Academy of Sciences USA, 1981, vol. 78, pp. 7535–7539.
Waterfield et al, Journal of Cellular Biochemistry, 1982, vol. 20, pp. 149–161.
Liebermann et al., J. Cell Science Supplement, 1985, vol. 3, pp. 161–172.
Sato et al. Mol. Biol. Med. 1: 511–529 1983.
Masui et al. Cancer Res 44: 1002–1007 1984.
Murthy et al. Fed Proc. 45(6) 1574 1986.
Palombella et al. Biosis AN: BA83:95900; J Biol Chem 262(5) 1950–1954 1987.
Bernstein et al. Proc. Am. Assoc. Cancer Res Ann Mtg vol. 28(0) 1987 p. 24.
Epenetos et al. British Med. J. 290:1463–66, 1985.
Murthy et al. Arch Biochem Biophys 252(2): 549–60 1987.
Houghton et al. Seminars in Oncology 13: 165–179, 1986.
Brody et al. Radiat. Ther. Oncol. 24:151–160, 1990.
Harris et al. Tibtech vol. 11:42–44, 1993.
Dorland's Illustrated Medical Dictionary, 25th Ed., W. B. Saunders, Publ. 1965, p. 651.
DeNardo et al. J. Radiation Oncol. Biol. Phys. 11:335–48, 1985.
Wessels et al. Med Phys. 11:638–645, 1984.
Sehlom, Ch6 in "Molecular Foundations of Oncology", Broder, Ed., Williams & Wilkins Publ., 1991 pp. 95–134.

*Primary Examiner*—Paula K. Hutzell
*Attorney, Agent, or Firm*—Banner & Allegretti, Ltd.

[57] ABSTRACT

Monoclonal antibody 425 having properties particularly beneficial for anti-tumor therapy has been raised. MAb 425 antibody binds to EGF-receptors and inhibits their bioactivities. The amount of binding of the antibody to cancer cells can be increased by treatment of the cells with lymphokine preparations. Radiolabeled MAb 425 is used for treatment of EGF receptor-expressing gliomas.

1 Claim, 8 Drawing Sheets

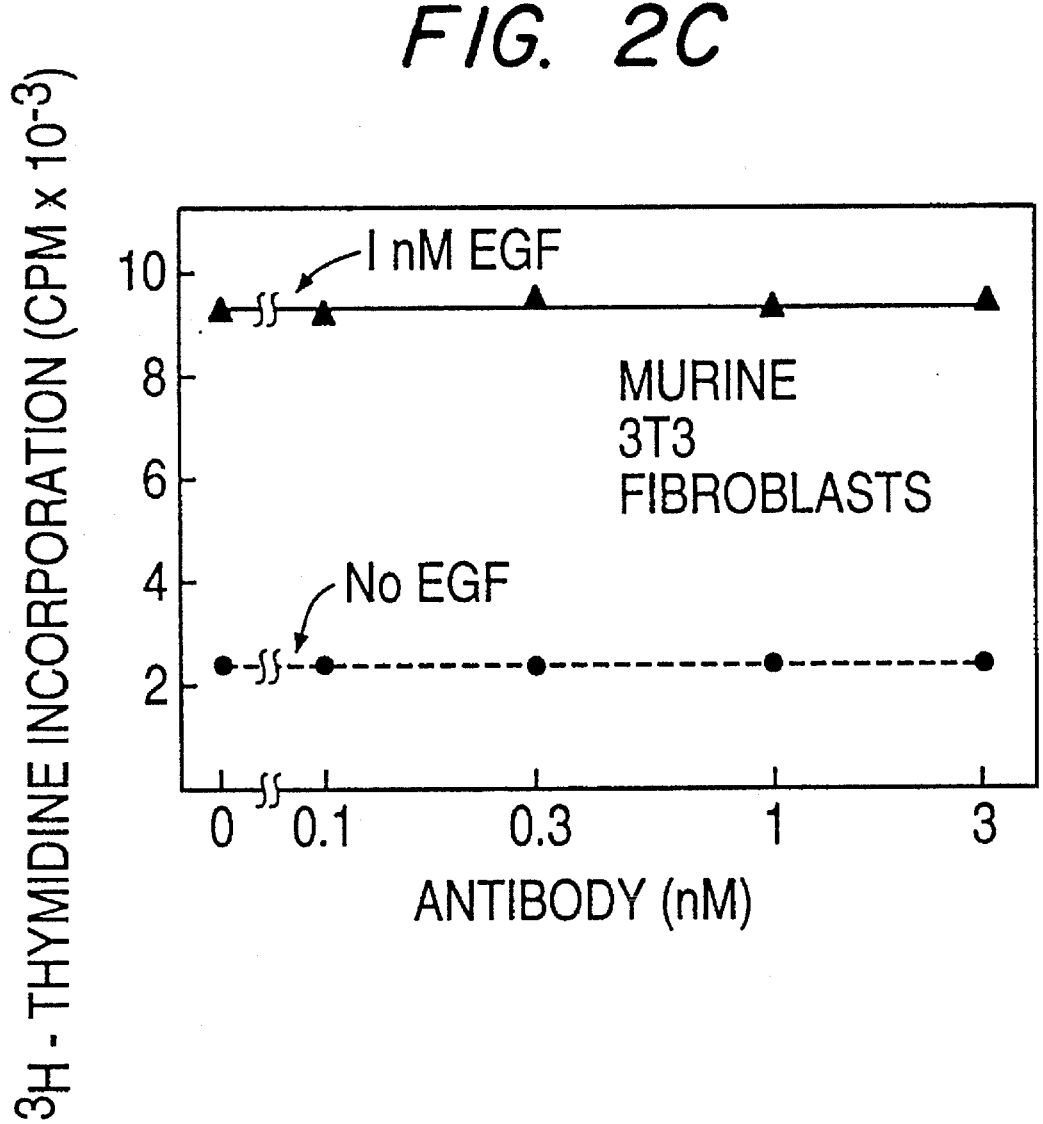

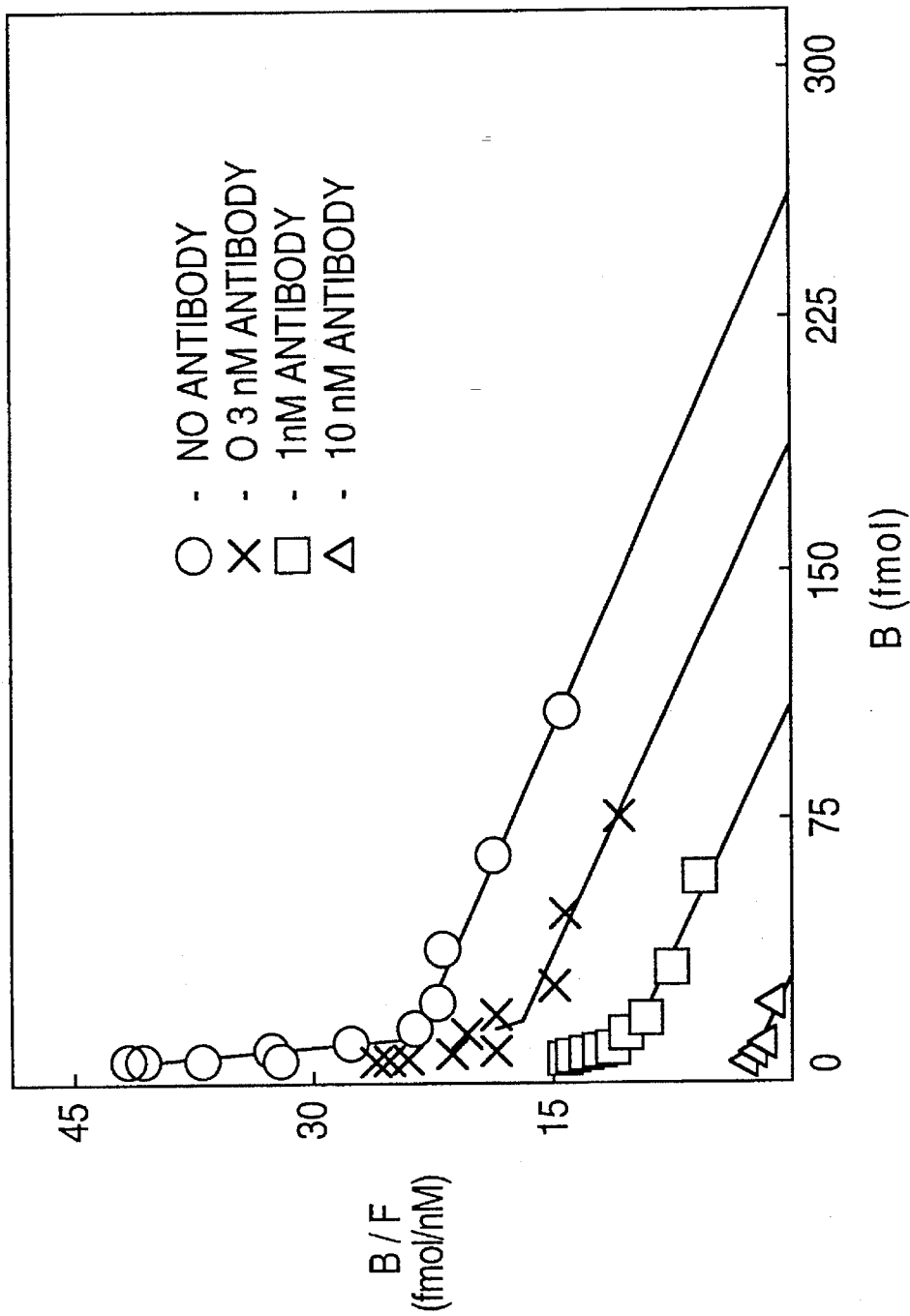

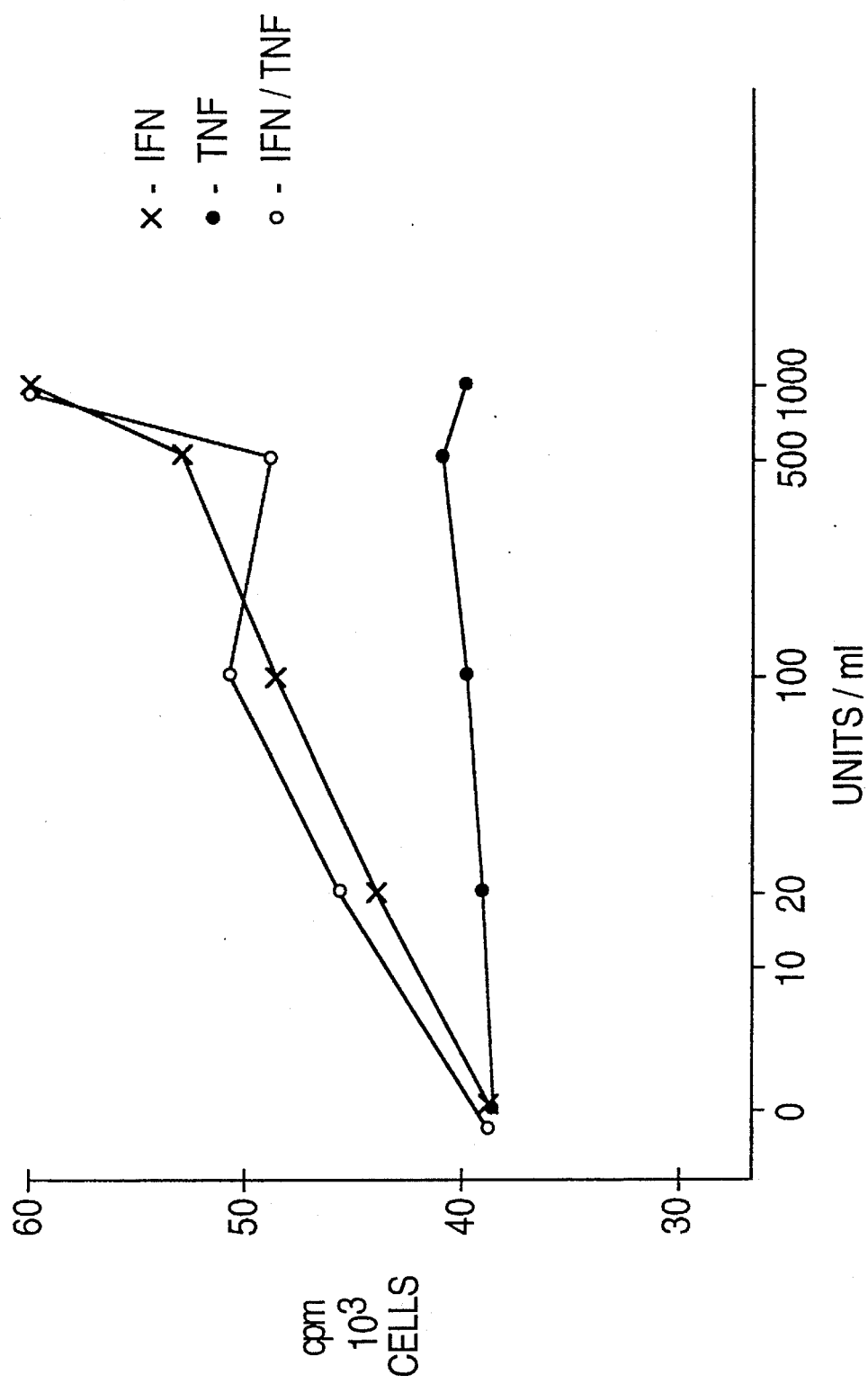

METHOD OF TREATING HUMAN EGF RECEPTOR-EXPRESSING GLIOMAS USING RADIOLABELED EGF RECEPTOR-SPECIFIC MAB 425

The U.S. Government has a paid-up license in this invention and the right in limited circumstances to require the patent owner to license others on reasonable terms as provided for by the terms of grant number CA25874 awarded by the National Institutes of Health. This application is a continuation of application Ser. No. 149,100 filed Jan. 27, 1988 now abandoned.

TECHNICAL FIELD OF THE INVENTION

The invention is in the field of cancer therapy. More particularly the invention relates to anti-tumor antibodies.

BACKGROUND OF THE INVENTION

Epidermal growth factor (EGF) is a polypeptide hormone which is mitogenic for epidermal and epithelial cells. When EGF interacts with sensitive cells, it binds to membrane receptors; the receptor EGF complexes cluster and then are internalized in endocytotic vesicles. This is responsible for the phenomenon of "down-regulation". EGF binding induces a tyrosine kinase activity of the receptor molecule and induces synthesis of DNA.

The EGF-receptor is a transmembrane glycoprotein of about 170,000 Daltons. (Cohen, *J. Biol. Chem.*, Vol. 258, pp. 1523–1531, 1982.) It is the gene product of the c-erb-B proto-oncogene. (Downward, et al., *Nature*, Vol. 307, pp. 521–527, 1984.) The receptor exists in two kinetic forms: so-called, low affinity and high-affinity receptors. These may be interconvertible. (Fernandez-Pol, *Biol. Chem.*, Vol. 260, pp. 5003–5011, 1985.)

The A431 carcinoma cell line expresses abundant EGF-receptors on its cell surfaces, and thus has been used in many studies to generate anti-EGF-receptor antibodies. However, the receptors on A431 differ from those of other cell types in the carbohydrate moieties attached to the polypeptide. Thus many antibodies raised against A431 membranes are directed against carbohydrates which are not common to all forms of the receptor molecule. (See, for example, *Richert, Fed. Proc.*, Vol. 42, p. 1094, 1983, Schreiber, *J. Biol. Chem.*, Vol. 258, pp. 846–853, 1983, *Gooi, Bioscience Reports*, Vol. 3, pp. 1045–1052, 1983, Vol. 5, pp. 83–94, 1985 and *Molecular Immunology*, Vol. 22, pp. 689–693, 1985.)

Others have generated monoclonal antibodies which are reactive with the protein moiety of EGF-receptors. These antibodies display a variety of properties upon binding to EGF-receptors, presumably dependent on the particular portion of the receptor molecule bound, and the isotype of the antibody. Some antibodies mimic some of the effects of EGF (agonists) and some inhibit the effects (antagonists).

Expression of EGF-receptors has been implicated in the progression of tumor growth. The gene for the receptors has been found to be the cellular analogue of the arian vital oncogene v-erb-B. (Ullrich, et al, *Nature*, Vol. 309, pp. 418–425, 1984.) In addition, an association has been detected between late stages of melanoma development and extra copies of the chromosome carrying the receptor gene. (Koprowski, et al., *Somatic Cell and Molecular Genetics*, Vol. 11, pp. 297–302, 1985.)

Because EGF receptors are expressed on a wide variety of solid tumors they provide a suitable target for anti-tumor therapy. However, there is a need in the art for a suitable anti-receptor antibody. Many of the known antibodies have properties which would be deleterious if used as anti-tumor agents. For example, antibodies which mimic the effects of EGF could stimulate the progression of the tumor rather than arresting it. Other antibodies which only bind to high or low affinity receptors could be less than optimally effective because EGF could still exert its effect through the unbound receptors. Still other antibodies convert low affinity receptors to high affinity receptors, which could exacerbate tumor growth rather than inhibiting it. Thus there is a need in the art for an anti-EGF-receptor antibody which would be suitable for anti-tumor therapy.

SUMMARY OF THE INVENTION

It is an object of the invention to provide a monoclonal antibody which binds to receptors for EGF and inhibits both high and low affinity binding of EGF.

It is another object of the invention to provide an antibody which inhibits the effects of EGF on sensitive cells.

It is yet another object of the invention to provide an antibody which inhibits phosphorylation of the EGF receptor.

It is still another object of the present invention to provide a method of treating human patients having solid tumors with anti-EGF receptor antibodies.

It is still another object of the invention to provide a method of treating human patients having solid tumors with lymphokines and anti-EGF receptor antibodies.

It is yet another object of the invention to provide a diagnostic method for solid tumors using antibodies raised against EGF-receptors.

These and other objects of the invention are provided through one or more of the following embodiments. In one embodiment, a monoclonal antibody is provided which has the following properties: (a) binds to human EGF-receptors; (b) inhibits both low and high affinity binding of EGF to EGF-receptors; (c) inhibits the EGF-dependent tyrosine kinase activity of EGF-receptors; (d) inhibits the growth of EGF-sensitive cells at a concentration of greater than 1 nM.

In another embodiment a cell line which produces the anti-EGF-receptor antibody is provided.

In still another embodiment a method is provided wherein patients with solid tumors are treated to arrest tumor growth. The method comprises the step of administering monoclonal antibodies to the patients. The antibodies have the ability to bind to the EGF receptor, to inhibit both low and high affinity binding of EGF to the receptors, to inhibit the tyrosine kinase activity of EGF receptors, and to inhibit the growth of EGF-sensitive cells at a concentration greater than 1 nM.

In yet another embodiment a method is provided where a lymphokine preparation is administered to a patient to induce enhanced expression of EGF-receptors on the surface of tumor cells, in conjunction with monoclonal anti-EGF receptor antibody administration.

In still another embodiment of the present invention a diagnostic method is provided in which radiolabelled F(ab')$_2$ fragments are prepared from the monoclonal antibodies of the present invention, and administered to patients. The location and size of the tumor are determined by gamma-scintigraphy to detect the radiolabelled F(a')$_2$ fragments.

The methods and antibodies of the present invention provide the art with a new and potent anti-tumor therapy. It is applicable to a wide range of solid tumors and avoids the need for radioisotopes. The latter benefit is especially desirable in the treatment of children. The antibodies can also be used in a radiolabelled form, both therapeutically and diagnostically.

BRIEF DESCRIPTION OF THE DRAWINGS

FIGS. 2A–C show the inhibiting effect of 425 antibody on EGF- induced DNA synthesis in quiescent (A) human foreskin, (B) human WI-38, and (C) murine 3T3 fibroblastic cells.

FIG. 4 depicts the effect of 425 antibody on the binding of EGF to A431 membranes.

FIG. 5 depicts the effect of lymphokine preparations on the expression of EGF-receptors in SW116 colorectal carcinoma cells.

DETAILED DESCRIPTION

Figure 1:
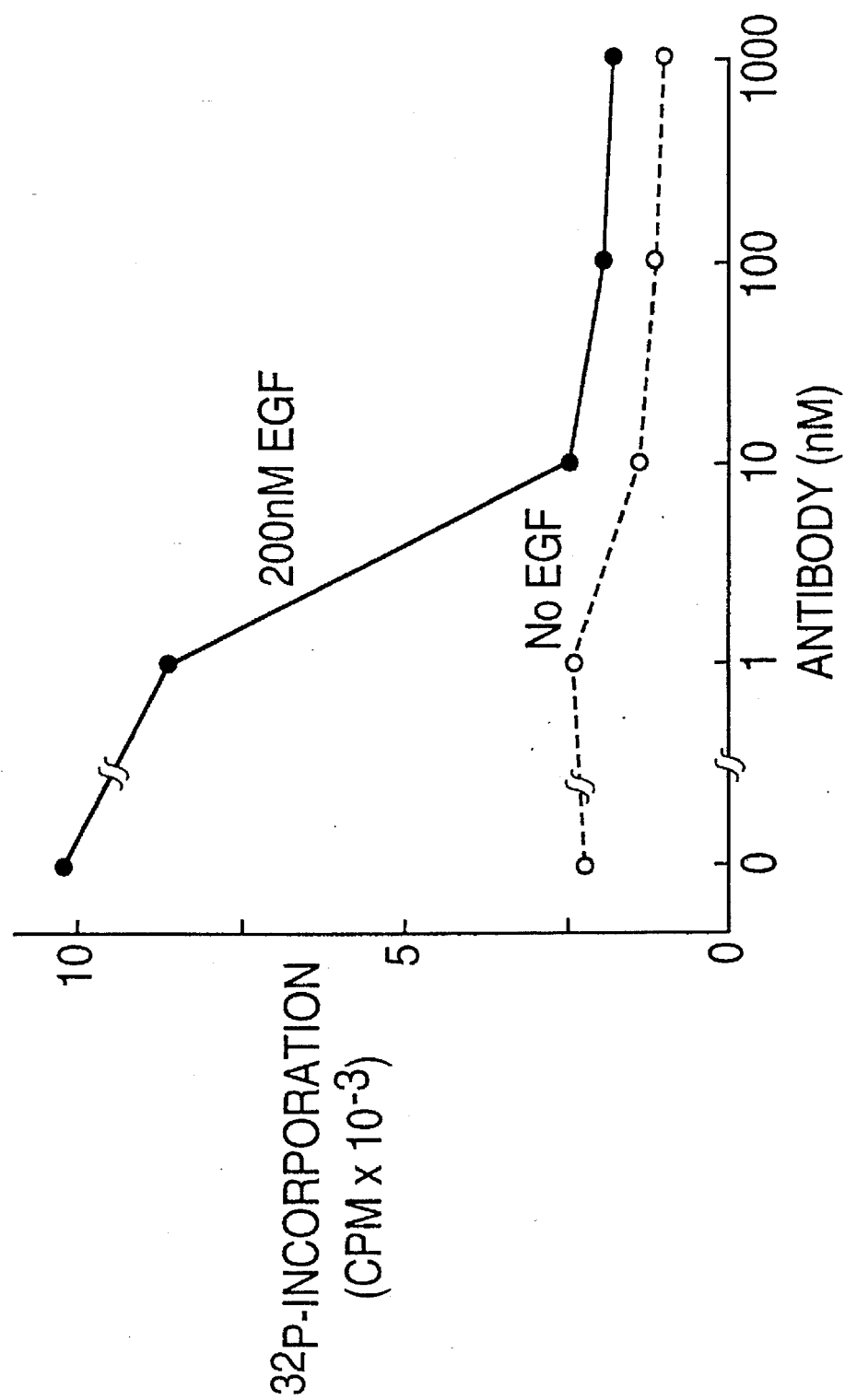
FIG. 1 shows the inhibitory effect of 425 antibody on autophosphorylation of EGF-receptor.

The present invention provides a monoclonal antibody which immunoprecipitates EGF-receptors. This binding interaction between the antibody and antigen occurs both in the presence and in the absence of the hormone EGF, suggesting that the binding of antibody occurs in a site distinct from the hormone binding site of the receptor. However, the antibody binding site is probably close to the hormone binding site, as the antibody inhibits binding of the hormone to the receptor.

Two populations of EGF-receptors have been defined, based on their binding affinities for hormone: so-called high and low affinity receptors. The antibodies of the present invention bind to both types of receptors and inhibit hormone binding to both types of receptors. It has been suggested that the high affinity receptors are the population responsible for mediating the mitogenic response of cells to EGF. (Kawamoto, *Proc. Nat'l. Acad. Sci. U.S.A.*, vol. 80, pp. 1337–1341, 1983.) Thus the ability of the antibody of the present invention to bind and inhibit those receptors could be the basis of their cytostatic effect.

The antibodies of the present invention inhibit the EGF-induced synthesis of DNA in quiescent human fibroblasts. No such inhibition is seen on murine fibroblasts. Thus the antibodies provided are apparently species specific.

The antibodies of the invention inhibit EGF-induced autophosphorylation of the EGF receptor. In the absence of EGF there is a basal level of phosphorylation which the antibodies do not effect appreciably. However, the phosphorylation which is induced by EGF is dramatically reduced by the antibody. For example, preincubation of receptors with 10 nM antibody, reduced the amount of autophosphorylation induced by 200 nM EGF by about 70%.

The binding site of antibodies of the invention on the receptor has been localized to one of the three trypsin generated fragments. The three fragments produced by limited trypsin proteolysis are about 17, 42, and 100 KDa and correspond to the autophosphorylation locus, the tyrosine kinase domain, and the hormone binding domain, respectively. The largest fragment is specifically immunoprecipitated by the antibodies of the invention. The antibody also binds to a 100 KDa form of the receptor which is secreted by A431 cells as the product of a truncated gene. This short and soluble receptor binds hormone but has no kinase site. (Weber et al, *Science,* Vol. 224, pp. 294,298, 1984).

Analysis of binding of the antibodies to A431 membranes indicates that there are two binding components, one high-affinity and one low-affinity. There are about 40-fold fewer of the high-affinity sites than the low-affinity sites, but their binding affinity is about 10,000-fold higher. The antibodies do not change the affinity of the receptors for EGF, but do reduce the number available for binding.

Antibodies of the above description can be produced using cell line 425 deposited at the American Type Culture Collection, 12301 Parklawn Drive, Rockville, Md., 20852 as Accession No. HB 9629 on Jan. 26, 1988. Growth of the cell line in vitro, using standard methods, produces a culture supernatant containing the appropriate antibodies. Alternatively the cells can be grown in vivo in nude mice and the ascites fluid collected. Both methods are well known to those of ordinary skill in the art.

The antibodies can be administered to human patients for therapy or diagnosis according to known procedures. Typically the antibody, or antibody fragments, will be injected parenterally, preferably intraperitoneally. However, the monoclonal antibodies of the invention can also be administered intravenously. In some cases immunosuppression of the patient may be desirable to minimize any adverse reaction toward the injected antibodies.

Determination of appropriate titers of antibody to administer is well within the skill of the art. Generally, the dosage ranges for the administration of the monoclonal antibodies of the invention are those large enough to produce the desired tumor suppressing effect. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from 0.1 mg/kg to 70 mg/kg, preferably 0.1 mg/kg to 500 mg/kg/dose, in one or more doses administrations daily, for one or several days.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

For diagnostic purposes the antibody can be conjugated to a radio-opaque dye or can be radiolabelled. A preferred labelling method is the Iodogen method. Fraker et al, *Blochem. Biophys. Res. Commun.,* Vol. 80, p. 849–857, 1978. Preferably the antibody will be administered as F(ab')$_2$ fragments for diagnostic purposes. This provides superior results so that background subtraction is unnecessary. Fragments can be prepared by known methods. See, e.g., Herlyn et al, *Cancer Research*, Vol. 43, pp. 2731–35, 1983. Generally, pepsin digestion is performed at acid pH and the fragments are separated from undigested IgG and heavy chain fragments by Protein A- Sepharose™ chromatography.

For therapeutic purposes the antibody can be conjugated to a toxin such as ricin subunit A, diptheria toxin, or a toxic enzyme. Alternatively it can be radiolabelled according to known methods in the art. However, the antibody of the present invention displays excellent cytotoxicity, in the absence of toxin, in the presence of effector cells, i.e. human monocytes.

Solid tumors which can be detected and treated using the present methods include melanoma, glioma and carcinoma. Cancer cells which do not highly express EGF-receptors can be induced to do so using lymphokine preparations. Also lymphokine preparations may cause a more homogeneous expression of EGF receptors among cells of a tumor, leading to more effective therapy.

Lymphokine preparations suitable for administration include interferon-gamma, tumor necrosis factor, and combinations thereof. These can be administered intravenously. Suitable dosages of lymphokine are 10,000 to 1,000,000 units/patient.

The following examples illustrate the general principles of the invention, but do not limit its scope.

EXAMPLE 1

This example illustrates the production of monoclonal antibody.

A Balb/c mouse was injected intraperitoneally with $2 \times 10^7$ A431 cells and phosphate-buffered saline (PBS). Twenty-five days later the mouse was reinjected intravenously with $2 \times 10^6$ A431 cells and PBS. On the third day following the second injection, the spleen was removed and the cells were fused with P3×63Ag8.653 mouse myeloma cells. (See, Kohler et al, *Nature*, Vol. 256, pp. 495–497, 1975; and Koprowski et al, *Somatic Cell Genetics*, Vol. 5, pp. 957–972, 1979.) The fusion products were grown in Dulbecco's modified Eagle's (DME) medium containing 20% fetal bovine serum (FBS) and hypoxanthine/aminopterin/thymidine.

The hybridoma supernates were screened for binding to A431 cells using a mixed hemeadsorption assay. (Herlyn, et al, *Proceedings of the National Academy of Sciences U.S.A.*, Vol. 76, pp. 1438–1442, 1979.) Supernates from positive clones were tested for inhibition of $^{125}$I-EGF binding to A431 cells. Hybrids whose supernates inhibited EGF binding were cloned twice and then maintained in the above medium. The antibody (No. 425) was purified from ascitic fluid produced in Balb/c mice using Protein A-Sepharose columns. It was established that the antibody class was $IgG_{2a}$ by indirect radioimmunoassay. (Herlyn et al, *Cancer Research*, Vol. 45, pp. 5670–76, 1985.)

EXAMPLE 2

This example demonstrates the inhibitory effect of 425 antibody on kinase activity of the EGF receptor as measured by autophosphorylation.

Solubilized receptor (about 30 ng, based on EGF binding ability) was subjected to the following successive treatments; (a) incubation at 4° C. for 60 minutes with or without 425 antibody in 15 ul of 20 mM Hepes, 10% glycerol, pH 7.4, 0.2% Triton X-100; (b) incubation at 4° C. for 10 minutes with or without 1 ul of 15 uM EGF. Phosphorylation was initiated by the addition of 5 ul of a solution containing 60 uM gamma-$^{32}$P-ATP (100 cpm/fmol) and 4 mM $MnCl_2$. After incubation at 4° C. for 30 minutes the reactions were terminated and the samples were subjected to SDS-polyacrylamide gel electrophoresis and autoradiography.

The extent of receptor phosporylation was quantified by measuring the radioactivity in the region of the dried gel containing the receptor band. Dried gel strips of similar dimensions from adjacent regions were counted to correct for background radioactivity. The results are shown in FIG. 1. The EGF-induced kinase activity of the solubilizied human receptor, measured as the extent of autophosphorylation, was blocked by the antibody.

EXAMPLE 3

The example shows the inhibitory effect of antibody 425 on EGF-induced DNA synthesis in quiescent fibroblastic cells.

Figure 2A:
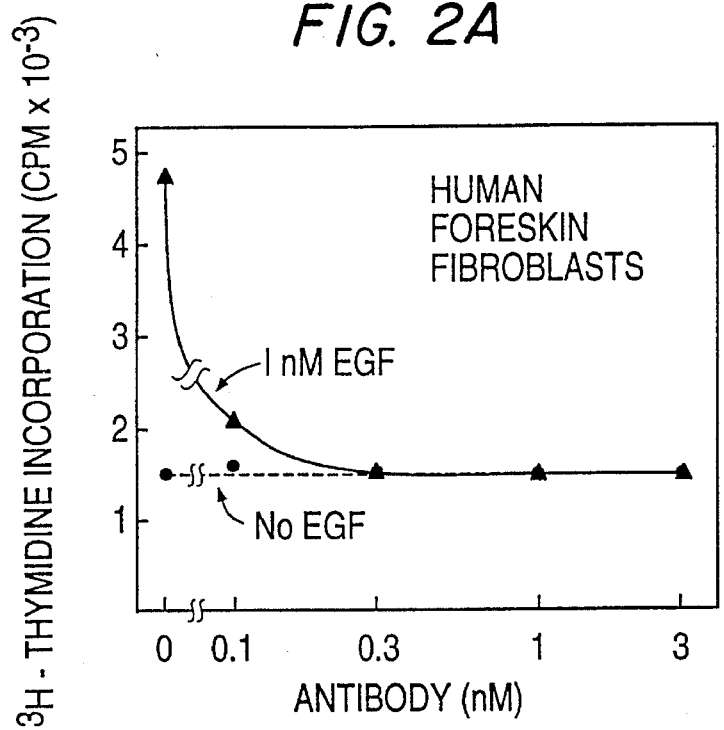
Figure 2B:
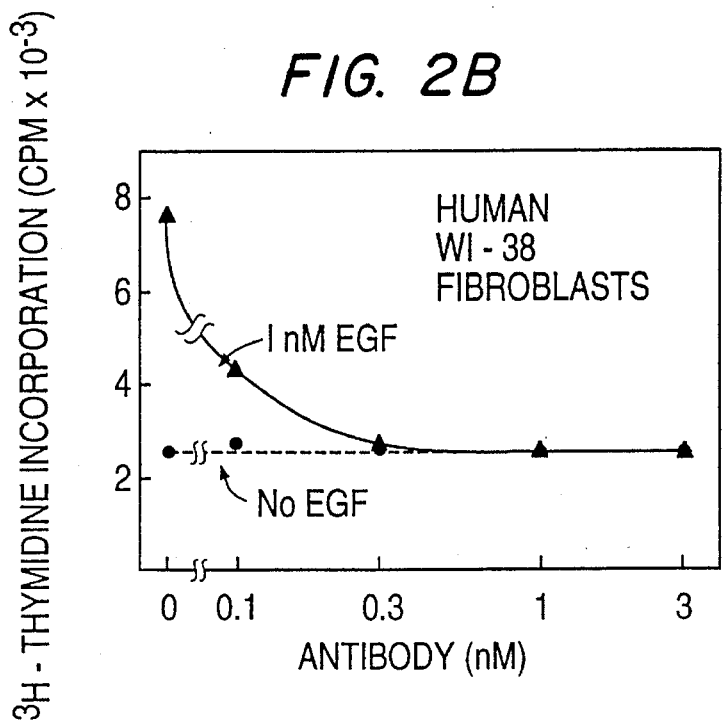

Human foreskin fibroblasts, human WI-38 fibroblasts, and murine 3T3 fibroblasts were tested. Cells were plated in 16-mm dishes at a denisty of $10^5$ cells per well in 1 ml of DME medium contain 10% FBS. After 24 hours at 37° C. the medium was replaced with 1 ml of DME medium containing 1% platelet-poor plasma. After 5 days at 37° C. these cells were preincubated with 425 antibody at 24° C. for 30 minutes in 0.3 ml of DME-medium containing 1% FBS. Then EGF was added and the monolayers were incubated at 37° C. At 18 hours after EGF addition, tritiated thymidine (1.5 Ci/mmol) was added to a final concentration of 1 uCi/ml and the incubations were continued at 37° C. for an additional 6 hours. Trichloroacetic acid insoluble radioactivity was determined. As can be seen in FIG. 2, the antibody was found to inhibit EGF-dependent DNA synthesis in both types of human fibroblastic cells, but not in the mouse 3T3 cell line.

EXAMPLE 4

This example demonstrates the phenomenon of down-regulation of the EGF receptor in human fibroblastic cells induced by the 425 antibody.

Human WI-38 fibroblasts and human foreskin fibroblasts were first incubated with antibody at 4° C. for a time long enough for binding equilibrium to be achieved, and then the cell dishes were transferred to 37° C. to allow endocytosis and down-regulation to occur. Subsequently, the dishes were washed extensively with antibody-free medium, and the extent of down-regulation (i.e., loss of surface receptor activity) was quantitated by determining EGF binding activity at 4° C. for 2 hours using a saturating concentration of $^{125}$I-EGF.

Monolayers of cells in 35-mm dishes were incubated at 4° C. for 2 hours with 1 nM 425 antibody in 1 ml of DME medium containing 1 mg/ml BSA (DME-BSA). then the dishes were transferred to 37° C.; at the indicated times of incubation at 37° C., the dishes were transferred to ice, washed extensively with ice-cold DME-BSA and then incubated at 4° C. for 2 hours with 40 nM $^{125}$I-EGF ($10^6$ cpm/pmol) in 1 ml of DME-BSA.

Figure 3A:
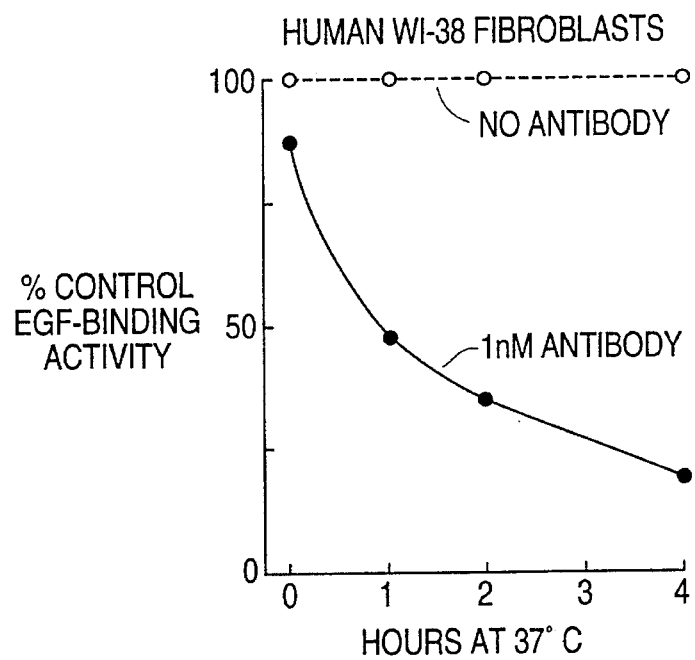
FIGS. 3A and 3B depict the 425 antibody-induced down-regulation of the EGF receptor in human (A) colorectal and (B) epidermoid carcinoma fibroblastic cells.
Figure 3B:
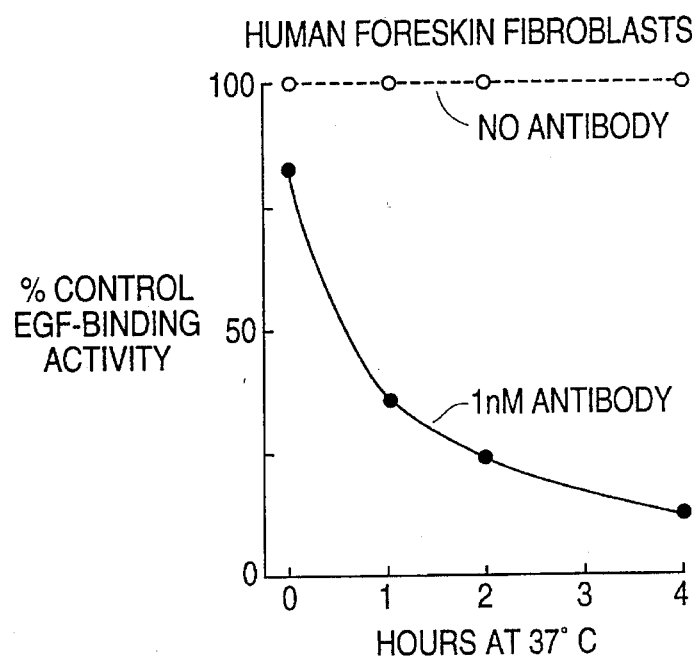

The results in FIG. 3 show the percentage of the control binding in cells at various times of 37° C. incubation with antibody. Control cells underwent identical treatment except for the absence of antibody. One hundred percent binding represents the specific binding of a 150 and 110 fmol $^{125}$I-EGF to WI-38 and foreskin fibroblasts, respectively. Nonspecific binding was 4000 and 7500 cpm for WI-38 and foreskin fibroblasts, respectively.

EXAMPLE 5

This example depicts the effect of 425 antibody on the equilibrium binding of EGF to A431 membranes.

Isolated membranes were prepared according to the method of Biswas, Biochemistry, Vol. 24, pp. 3795–3802, 1985. The membranes were preincubated at 4° C. for 1 hour with or without 425 antibody. The membranes were then incubated at 20° C. for 1 hour with $^{125}$I-EGF in 15 ul of 20 mM Hepes, pH 7.4/0.15M NaCl (Hepes/NaCl) containing 1 mg/ml BSA. At the end of the incubation 1 ml of ice-cold Hepes/NaCl was added, and the suspension was passed through Millipore™ EGWP 0.2-um pore filters. The filters are washed three times with Hepes/NaCl and assayed for radioactivity in a gamma-counter. Nonspecific binding was determined in the presence of 5 uM unlabeled EGF.

Scatchard analysis of EGF binding to A431 membranes shows that in the presence of antibody, there is a reduction in the number of both high and low affinity EGF binding sites. There is no alteration in the binding affinity. These results suggest that the antibody can bind to both high and low affinity EGF receptors. The binding of the antibody to the high-affinity receptors is of interest because these receptors may represent the mitogenically active entities.

EXAMPLE 6

This example shows the effect of lymphokine preparations on the expression of EGF receptors in SW 116 colorectal carcinmoa cells.

Expression of EGF receptors was tested with $^{125}$I-labelled monoclonal antibody 425. The antibody was labelled by mixing 5 ug of purified antibody with carrier-free Na$^{125}$I (0.5 mCi) in 0.1M potassium phosphate buffer, pH 7.5 (total volume 10 ul). 10 ul of chloramine T (2 mg/ml) were added and mixed for 1 minute at 24° C. The reaction was terminated by the addition of 10 ul of 4 mg/ml sodium metabisulfite (4 mg/ml) and 10 ul of KI (70 mg/ml). The labelled protein was separated from unreacted Na $^{125}$I by gel filtration through Sephadex™ G-15. The buffer used for diultion contained 10 mM Tris-HCl pH 7.4, 0.15M NaCl, and 1 mg/ml bovine serum albumin. The specific radioactivity of the preparation was about 100,000 cpm/ng protein.

FIG. 5 shows the effect on cells which were cultured for 72 hours in the presence of various concentrations of interferon-gamma, tumor necrosis factor, or a combination of both. Results are expressed as cpm/10$^3$ cells.

EXAMPLE 7

This example depicts the 425 antibody binding to A431 membranes.

Membranes either were pretreated with EGF, or were left untreated, and then incubated at 20° C. for 1 hour with radioiodinated 425 antibody in Hepes/NaCl containing 1 mg/ml BSA. Membrane-bound radioactivity was determined after filtration through Millipore™ filters as described above. Nonspecific binding was determined in the presence of 0.3 uM unlabelled antibody.

Figure 6:
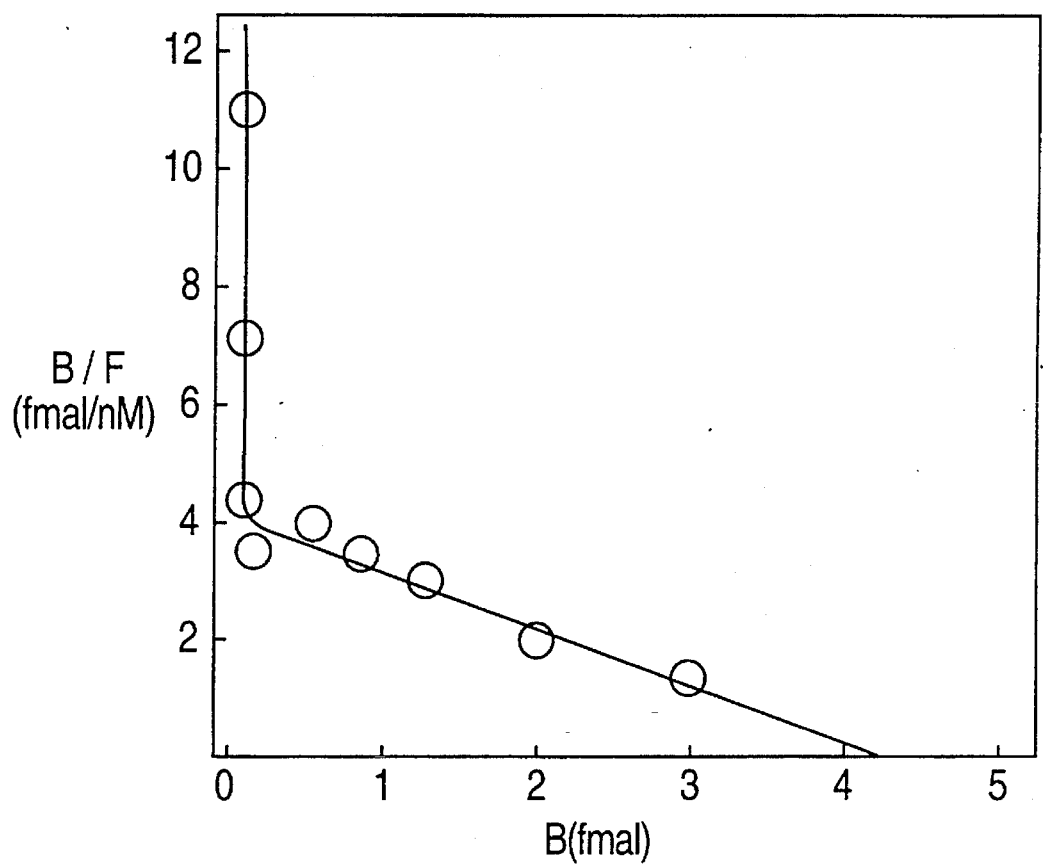
FIG. 6 depicts 425 antibody binding to A431 membranes.

Binding of radioiodinated antibody to A431 membranes was specific and saturable, as can be seen in FIG. 6.

Scatchard analysis revealed the presence of two binding components, a high-affinity, low-capacity component ($K_d$ about 10 pM; about 5×10$^8$ sites/ug membrane protein,) and a relatively low-affinity, high-capacity component ($K_d$ about 1 nM; about 2×10$^{10}$ sites/ug membrane protein). The estimated number of antibody binding sites in these membranes is roughly equal to the number of EGF binding sites. Also the concentration of labelled antibody required for half saturation of the binding sites of A431 membranes is the same as that needed for half-maximal inhibition of EGF binding to these membranes. These results reconfirm that the antibody binds only to the EGF receptor and to no other membrane molecule.

EXAMPLE 8

This example demonstrates the lysis of tumor cells by monoclonal antibody 425 in tissue culture in the presence of effector cells.

In antibody-dependent, cell-mediated, cytotoxicity assays using either human monocytes, lymphocytes or murine macrophages, antibody 425 mediated tumor cell lysis of two EGF-receptor positive cell lines SW 948 and A431. The results are shown below in Table 1.

| | | % of specific cytotoxicity[b] | | |
|---|---|---|---|---|
| | Number of binding | Human | | Mouse |
| Cell line | sites/cell[a] | monocytes | lymphocytes | macrophages |
| A 431 | 1 × 10$^6$ | 49.7 | 30.4 | 57.2 |
| SW 948 | 5 × 10$^4$ | 12.5 | 6.8 | 30.1 |

MAb 425-dependent cell-mediated cytotoxicity with human and murine effector cells

[a]Number of binding sites determined by Scatchard analysis.
[b]Results are expressed as mean % cytotoxicity of duplicate samples, which varied <10% and are corrected for unspecific cytotoxicity induced by MAbs not binding to target cells (anti-influenza virus-antibodies H24B5 and H35-85-5); range of non-specific cytotoxicity 2–19%.

A431 cells which show high receptor density, were lysed to a greater extent than SW 948 cells, by both human and mouse effector cells in the presence of monoclonal antibody 425. These results suggest that cells with more binding sites are destroyed more efficiently than those with fewer binding sites.

EXAMPLE 9

This example demonstrates the inhibition of tumor growth in nude mice by monoclonal antibody 425.

Figure 7A:
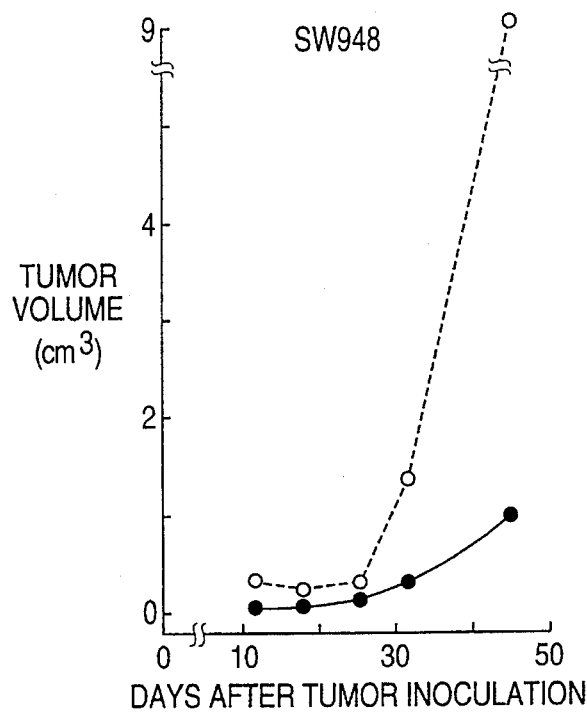
FIGS. 7A and 7B shows the effect of antibody 425 on growth of human (A) colorectal and (B) epidermoid carcinoma tumors on nude mice.
Figure 7B:
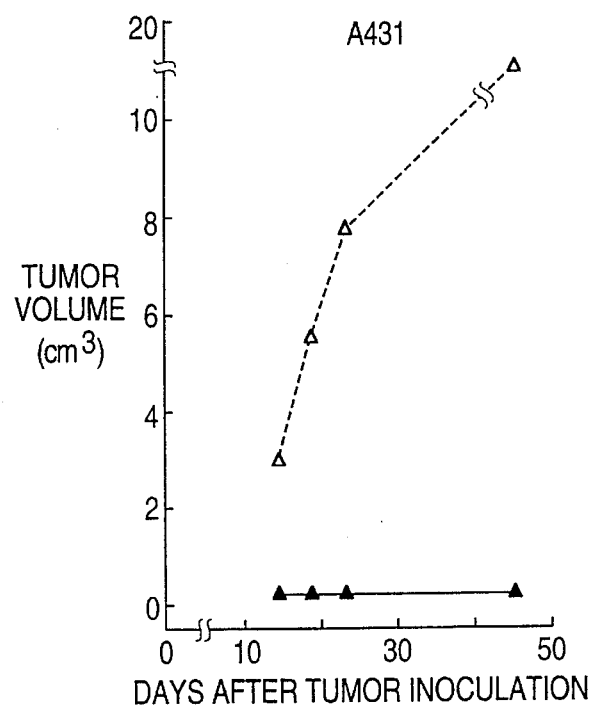

Nude mice was xenografted with either SW 948 or A431 cells by subcutaneous inoculation. SW 948 cells are colorectal carcinoma cells and A431 cells are human epidermoid carcinoma-derived cells. Antibody 425 or control anti-influenza virus monoclonal antibody were administered intraperitoneally, starting on the day of tumor inoculation and on days 1, 2, 3, 4, 7, 9, 11, 14, 16, and 18 thereafter. Tumor volumes were recorded once weekly for six weeks after inoculation. As shown in FIG. 7, tumor volumes of mice inoculated with SW 948 cells remained unchanged until day 28 after inoculation. From then on, tumor volumes increased but remained considerably smaller than those of control mice. In the mice xenografted with the A431 cells, tumor growth was completely inhibited during the observation period of 45 days.

In another set of experiments, one group of three nude mice was xenografted with $2\times10^6$ A431 cells received a single dose of 200 ug of antibody 425 at the time of tumor implantation. Another group of four mice received the first injection of 200 ug of monoclonal antibody 425 five days after implantation of $3\times10^6$ of A431 cells. Marked inhibition of tumor growth was observed in both groups of mice.

We claim:

1. A method of treating a human patient having an EGF-receptor-expressing glioma, comprising:
 administering MAb 425, which is produced by the cell line deposited at the American Type Culture Collection as Accession No. HB 9629, to the patient, wherein MAb 425 is radiolabelled.

* * * * *